United States Patent
Rao

(12) 
(10) Patent No.: US 6,379,692 B1
(45) Date of Patent: Apr. 30, 2002

(54) PHARMACEUTICAL COMPOSITION COMPRISING A SUSPENSION FOR THE ACTIVE INGREDIENT

(75) Inventor: Leburu Seshagiri Rao, Romford (GB)

(73) Assignee: Chauvin Pharmaceuticals Limited, Romford (GB)

( * ) Notice: Subject to any disclaimer, the term of this patent is extended or adjusted under 35 U.S.C. 154(b) by 0 days.

(21) Appl. No.: 09/145,900

(22) Filed: Sep. 2, 1998

(30) Foreign Application Priority Data

Sep. 3, 1997 (GB) ............................................. 9718568

(51) Int. Cl.$^7$ .......................... A61K 9/16; A61K 47/32; A61K 47/36; A61K 47/38

(52) U.S. Cl. ....................... 424/427; 424/490; 514/912; 514/951; 514/954

(58) Field of Search ................................. 424/490, 489, 424/427, 405; 514/912, 954, 951, 772.6, 777, 781

(56) References Cited

FOREIGN PATENT DOCUMENTS

| EP | 0533836 B1 | 2/1996 |
|---|---|---|
| GB | 2080106 | 2/1982 |
| GB | 2082455 | 6/1984 |
| GB | 2217595 | 11/1989 |
| GB | 2306885 | 5/1997 |
| WO | WO 91/02517 | 3/1991 |
| WO | WO 93/00887 | 1/1993 |
| WO | WO 93/01814 | 2/1993 |
| WO | WO 93/17664 | 9/1993 |
| WO | WO 95/26711 | 10/1995 |
| WO | WO 96/14830 | 11/1995 |
| WO | WO9843643 A | 10/1998 |

OTHER PUBLICATIONS

Database WPI, Section Ch, Week 9651, Derwent Publications Ltd., London, GB; AN 96–514906, XP002086520 & JP 08 268892 A (Yuwa Shogi), Oct. 15, 1996.

"Carbomer", from *Handbook of Pharmaceutical Excipients, 2nd Edition,* A. Wade and P.J. Weller, 71–73, The Pharmaceutical Press, London (1994).

*Primary Examiner*—Edward J. Webman
(74) *Attorney, Agent, or Firm*—Synnestvedt & Lechner LLP

(57) ABSTRACT

A pharmaceutical formulation may be prepared by a method comprising providing the active ingredient in solution in a pharmacologically-acceptable base and mixing the resulting solution with a pharmacologically-acceptable acid in an amount such that the formulation attains a pH in the range of from about 3.5 to about 8.5 to thereby precipitate out the active ingredients, a viscosity-enhancing agent having been incorporated in the formulation prior to or during the mixing with acid. The formulation is suitable for administration of a pharmacologically active ingredient which is sparingly soluble in water at a pH acceptable for administration, for example to the eye of the patient.

23 Claims, No Drawings

PHARMACEUTICAL COMPOSITION COMPRISING A SUSPENSION FOR THE ACTIVE INGREDIENT

The present invention relates to a method of preparing pharmaceutical formulations and to pharmaceutical formulations, particularly for ophthalmic use, which may be prepared by that method. In particular, the present invention relates to a method of preparing pharmaceutical formulations wherein the active ingredient is of sparing solubility in pharmaceutically-acceptable solvents.

There is a recurring problem of how to formulate pharmacologically active ingredients which exhibit low solubility in pharmacologically- and pharmaceutically-acceptable solvents at a pH acceptable for the intended use. It is particularly difficult to solve when the formulation is to be administered to a sensitive organ such as the skin or the eye and is required to be at a pH acceptable to the eye. Such ingredients can often only be formulated as ointments in acceptable carriers for pharmaceutical use, such as paraffin or as emulsions with suitable additives. In these instances it has not been found possible to formulate in aqueous and/or non aqueous formulations such as eye drops or gels of wider acceptability.

One such poorly-soluble, active ingredient is the drug aciclovir (formerly acyclovir; 2-amino-1,9-dihydro-9-[(2-hydroxyethoxy)methyl]6H-purin-6-one or 9-(2-hydroxyethoxymethyl)guanine) which is well-known for its antiviral properties especially against several Herpes viruses. Due to its low lipid and water solubilities, aciclovir is also of low bioavailability, further compounding the formulation problems. It is sold, for topical ocular application, in the form of a paraffin-based ointment, and, for dermal application, as a 5% aqueous emulsion incorporating a high content of propylene glycol.

However, to be of practical use for administration to the eye, an alternative formulation to such an ointment is required. Highly desirable would be a form of eye drops for ease of administration and use, and to increase bioavailability. However, with aqueous solubility of less than 0.1% w/v, it has not been possible to incorporate aciclovir as the active ingredient in eye drop formulations. For an alternative formulation to be medically and commercially successful, it would have to comprise an aqueous carrier in which the aciclovir were bioavailable to a degree that 1% aciclovir by weight of the total formulation could be administered 2–3 times per day, rather than a paraffinic formulation which requires 5 applications per day of a formulation having a high concentration (say, 3% w/w) of aciclovir.

Similar problems exist with other low solubility, low bioavailability antiviral drugs such as ganciclovir (2-amino-1,9-[[2-hydroxy-1-(hydroxymethyl)ethoxy]methyl]-6H-purin-6-one) which is especially effective in cases of cytomegalo virus retinitis. Penciclovir (9-[4-hydroxy-3-(hydroxymethyl) butyl] guanine) is another effective antiviral having low aqueous (and even lipid) solubility and low bioavailability.

If alternative formulations of these drugs were available which would be suitable, for example, for topical ocular administration, then they could also be modified (e.g. by increasing its viscosity) so as to be suitable for dermal application.

The present invention provides a method of preparing a pharmaceutical formulation suitable for administering to a patient in need thereof a pharmacologically active ingredient which is sparingly soluble in water at the pH acceptable for administration, comprising providing the active ingredient in solution in a pharmacologically-acceptable base and mixing the resulting solution with a pharmacologically-acceptable acid in an amount such that the formulation attains a pH in the range of from about 3.5 to about 8.5 to thereby precipitate out the active ingredients, a viscosity-enhancing agent having been incorporated in the formulation prior to or during the mixing with acid.

Preferably at least one ion-sensitive, hydrophilic polymer is also incorporated in the formulation prior to or during the mixing with acid, which polymer has been found to provide an additional viscosity-enhancer and enchance stability of the formulation.

It has been unexpectedly discovered that, by this method, formulations can be produced which are suspensions of appropriately-sized microparticles of active ingredient, suitably in an aqueous gel, and where the particle size is surprisingly evenly distributed throughout the suspension when compared to formulations prepared by suspending pre-micronized drug in an aqueous gel.

Furthermore, the method has the advantage that sterile conditions are relatively easy to maintain throughout because the microparticles are generated in situ, in contrast to a process involving physical micronization of the active ingredient and subsequent suspension where it is difficult to maintain sterility.

An example of an active ingredient suitable for formulation in accordance with the invention is aciclovir. In the case of aciclovir, using sodium hydroxide and hydrochloric acid as base and acid, on neutralization by the acid of the sodium aciclovir salt initially formed from aciclovir plus base, a precipitate of aciclovir is produced which is suspended in a sodium chloride solution.

However, without the use of a viscosity-enhancing agent, the aciclovir precipitates out as needle-shaped crystals having a length greater than 30 $\mu$m, and without the ion-sensitive polymer has an unacceptable tendency to sedimentation. Particularly for ocular use, the crystals are too long by a factor of about six, and too sharp. It was surprisingly found that incorporating a viscosity-enhancing agent, particularly prior to neutralization, produced acceptable crystal morphology. Furthermore, a formulation having appropriate stability (e.g. which does not sediment on standing to form a 'cake' which can not be resuspended or which has an unacceptable resuspension time), was produced by incorporating the ion-sensitive, hydrophilic polymer component, especially a cross-linked polyacrylic acid (also acting as a viscosity-enhancing agent), also preferably prior to the neutralization step.

Therefore, a preferred method in accordance with the invention comprises:

(i) dissolving the active ingredient in base to form a salt solution;

(ii) forming an aqueous suspension or dispersion of the ion-sensitive, hydrophilic polymer(s) and the viscosity-enhancing agent; and (iii) bringing the salt solution, the aqueous suspension or dispersion and the acid into admixture whereby there is formed a precipitate of microparticles of the active ingredient wherein 90% of the microparticles are of a diameter less than about 10 $\mu$m (number) when measured by a Coulter counter (100 $\mu$m tube).

Step (iii) may be undertaken by first bringing the salt solution into admixture with the aqueous suspension or dispersion followed by addition of the acid. However, preferably, the acid is added to the aqueous suspension/dispersion prior to addition thereto of the salt solution. Preferably, more base is then added to the suspension to neutralize the hydrophilic polymer(s). The resulting formulation is an aqueous gel having fine particles of precipitated active ingredient in aqueous suspension. It has been found that the mean size of particles of active ingredient produced according to the process of the present invention is of the order of 2–10 μm (number) or 4–16 μm (volume); preferably around 4 μm (number) or 8 μm (volume).

However, in contrast to when pre-micronized active ingredient is used, the process of the present invention whereby such fine particles are produced in situ by precipitation results in a better distribution of particle size, with the $D_{90}$ at room temperature being of the order of 5–10 μm (number), preferably 7–9 μm (number) or 10–16 μm (volume), whereas for pre-micronized drug the $D_{90}$ is of the order of 5–10 μm (number) or 21–24 μm (volume). The formulations of the present invention exhibit similar $D_{90}$ values at room temperature for the initial formulation and also after storage for up to 18 months. The term "$D_{90}$" as used herein with respect to particle size distribution means that 90% of the particles have a diameter, when measured by a Coulter counter (100 μm tube), of less than the quoted figure. Unless otherwise stated, all measurements are taken at room/ambient temperature.

Therefore a further preferred method in accordance with the invention, for preparing a suspension of microparticles of an active ingredient in an aqueous gel, comprises:

(i) dissolving the active ingredient in base to form a salt solution;

(ii) forming an acidic dispersion of an ion-sensitive, hydrophilic polymer and a viscosity-enhancing agent in an acid; and (iii) mixing the salt solution with the acidic dispersion to produce a precipitate of particles of active ingredient having a particle size $D_{90}$ less than about 16 μm (volume); and (iv) adding sufficient base to produce an aqueous gel having a pH in the range of from about 3.5 to about 8.5.

Conveniently, the active ingredient used in step (i) is non-micronized but, especially if readily commercially available, pre-micronized powder may also be used.

When used, a non-ionic surfactant is preferably added in the acidic dispersion with the ion-sensitive, hydrophilic polymer. Other ingredients such as a preservative or the like are preferably added after the mixing/neutralizing step.

The invention also includes pharmaceutical formulations when prepared by the method as described above.

The present invention also includes a pharmaceutical formulation which may be prepared by the above method and suitable for administering to a patient in need thereof a pharmacologically active ingredient which is sparingly soluble in water at the pH acceptable for administration, which formulation comprises:

(a) 0.1–5% w/w of the active ingredient;

(b) a viscosity-enhancing agent;

(c) a pharmacologically-acceptable base in which the active ingredient is soluble in an amount sufficient to dissolve substantially all of the active ingredient; and (d) a pharmacologically-acceptable acid in an amount such that the formulation has a pH in the range of from about 3.5 to about 8.5 and such that substantially all of the active ingredient precipitates out.

Preferably the formulation also includes 0.1 to 3% (preferably 0.05 to 3%) w/w of one or more ion-sensitive, hydrophilic polymer(s) and the base(c) is present in an amount sufficient both to dissolve substantially all of the active ingredient and to neutralize the ion-sensitive hydrophilic polymer(s).

The present invention further provides a pharmaceutical formulation comprising a suspension of particles of the active ingredient having a mean particle size in the range of from 2–10 μm (number) or 4–15 μm (volume) and a $D_{90}$ (as hereinbefore defined) of the order of 5–10 μm (number), preferably 7–9 μm (number) or 10–16 μm (volume) in an aqueous gel having a pH in the range of from about 3.5 to about 8.5.

The amount and type of viscosity-enhancing agent is chosen such that the viscosity of the final formulation is suitable for its chosen method of administration. For example, final viscosity may be in the range of from about 1000 to about 3500 cP, preferably about 2000–3000 cP, to enable, in the case of an ophthalmic formulation, administration in droplet form. On the other hand, for dermal application, a higher viscosity in the range of from about 5000 to about 10000 cP, preferably about 7000 cP, would be suitable. Increasing the viscosity in this way generates the required particle size of active ingredient and helps to maintain the stability of the particle size in the suspension. Suitable viscosity-enhancing agents include hydroxyalkylcelluloses (such as hydroxymethylcellulose, hydroxyethylcellulose, hydroxypropylcellulose and hydroxypropylmethylcellulose), and also hyaluronic acid and polyvinyl pyrrolidone, or mixtures thereof. A preferred viscosity-enhancing agent is sold under the tradename Natrosol, for example, Natrosol 250M Pharm. The viscosity enhancing agent is suitably present in the formulation in an amount in the range of from about 0.1 to about 3.0% w/w, preferably from about 0.3 to about 1.0% w/w, more preferably 0.5 to 1.0% w/w.

Preferably, the ion-sensitive, hydrophilic polymer(s) is or are one(s) which is/are acidic and form(s) a gel on neutralisation. Some may act as a viscolising (viscosity-enhancing) agent as well as functioning as a suspending agent for the particles of active ingredient in the formulation. The hydrophilic polymer thereby functions to prevent or substantially reduce sedimentation of the particles of active ingredient in the formulation. Particularly preferred ion-sensitive, hydrophilic polymers are therefore selected from those wherein the resulting gel has a yield value in excess of about 80 dynes/cm$^2$; more preferably, >90 dynes/cm$^2$; especially >100 dynes/cm$^2$ as measured at room/ambient temperature with a Brookfield viscometer (such as model no. RVTDV II) having a spindle speed of 20 rpm.

Suitable polymers therefore include cross-linked polyacrylic acid(s). Particularly suitable cross-linked polyacrylic acids are carbomers which are synthetic high molecular weight polymers of acrylic acid cross-linked with polyalkenyl ethers or divinyl glycol. Especially suitable are the Carbopol (registered trademark) resins, Pemulen (registered trademark) polymeric emulsifiers and Noveon (registered trademark) polycarbophils. Preferably, Carbopol polymers are used which are polymers of acrylic acid cross-linked with either allylsucrose or alkyl ethers of pentaerythritol; they contain in the range of from 56–68% of carboxylic acid groups (calculated on the dry basis). Especially preferred for use in the formulations of the present invention is Carbopol 974P, having a molecular weight of approximately 3 m, being a high purity grade of resin having excellent stability at high viscosity; its viscosity (0.5%, pH 7.5) is in the range of 29,400–39,400 cP. Alternatively, however, other ion-sensitive, hydrophilic polymers such as those which function as pH-sensitive gelling polymers could be used instead. Preferably, such polymers are present in an amount in the range of from about 0.1 to about 3.0, preferably about 0.3 to about 1.0% w/w, more preferably, about 0.4 to about 0.6% such as 0.45 or 0.55% w/w.

In the formulations of the present invention, the hydrophilic polymer(s), if present, is/are neutralized by, the base to produce a highly viscous gel. For this purpose, the base may comprise amino acids; borax; alkali metal hydroxides such as sodium or potassium hydroxide; and/or polar organic amines such as triethanolamine. One gram of carbomer, for example, is neutralized by about 0.4 g sodium hydroxide. However the other function of the base in these formulations is to form a soluble salt of the active ingredient. Preferred, therefore, are alkali metal hydroxides and carbonates which are pharmacologically acceptable, particularly for use in the eye. Especially preferred is to use sodium hydroxide resulting, in the case of the active ingredient being aciclovir, in a solution of sodium aciclovir.

The amount of acid to be included in these formulations is calculated both to ensure that a substantial portion of the active ingredient is precipitated out of the initially basic solution and in the light of the amount of base present, to ensure a final pH of the formulation in the range of 3.5 to 8.5, preferably about 7 (neutral). The term "neutralization" used herein is therefore to be construed accordingly. The acid chosen must be pharmacologically acceptable and result in a pharmacologically acceptable salt which will be formed in situ from the base. Suitable acids therefore include inorganic acids such as hydrochloric and phosphoric, and some organic acids such as acetic. Preferably, hydrochloric acid is used.

In addition to the above-mentioned ingredients, the formulations of the present invention may further comprise other pharmacologically-acceptable excipients. Preferably, there is included a non-ionic surfactant which, suitably, has a hydrophile-lipophile balance (HLB) in the range of from about 12 to about 20, more preferably about 14 to about 16. In general, the polysorbates are suitable, such as polysorbate 80, or any other non-ionic surfactant capable of coating the particles of active ingredient precipitated so as to help both maintain the particles in suspension and hinder crystal growth. Particularly preferred are those surfactants which aid wetting of the hydrophilic polymer(s). Suitable surfactants are sold under the trade names Pluronic, Span and Tween, such as Pluronic L64 and Tween 80, both having HLB=15. Conveniently, the amount of non-ionic surfactant in the formulation is in the range of from about 0.05 to about 0.2% w/w.

A preservative is present typically in the range of from 0–0.02% w/w of the formulation, preferably about 0.01%, such as benzalkonium chloride (for example, 0.02% of a 50% solution), chlorhexidine, cetrimide, disodium edetate (EDTA), the parabens, thiomersal, chlorbutanol or the like, or a mixture thereof. Other excipient(s) may be selected from buffering agents such as disodium hydrogen phosphate and/or sodium dihydrogen phosphate; tonicity-enhancing agents such as sorbitol, mannitol, glycerin, dextrose and the like; permeation-enhancing agents such as propylene glycol; and other pharmaceutically- and pharmacologically-acceptable excipients available in the art.

The formulations of the present invention are suitable for treating any condition for which the active ingredient is pharmacologically effective, in particular: ocular viral infections such as those instigated by Herpes simplex (epithelial and stromal keratitis; corneal ulcers; and kerato-uveitis); Varicella zoster (dendritic keratitis, uveitis and retinopathy); cytomegaloviruses (retinopathy) and adenoviruses (keratoconjunctivitis); and skin conditions such as those caused by Herpes simplex (genital herpes and cold sores) and Varicella zoster (shingles).

It will be appreciated that the pharmaceutical formulations, while primarily intended for human use, may also be suitable for veterinary use, so that the term "patient" is to be understood as including humans and animals.

While the invention has been found particularly effective for formulation of aciclovir, it can also be used for formulation of low solubility, low bioavailability antiviral drugs such as ganciclovir and penciclovir. Additionally the method of the invention my be applied to drugs for treating allergic reactions such as sodium cromoglycate which is soluble in alkali but precipitates at acidic pH (about pH 4) to give a fine insoluble material which can then be incorporated in formulations having a relatively prolonged action when used by the patient.

Similarly, a broad spectrum antibiotic such as cefuroxime the sodium salt of which is soluble at alkaline pH can be finely precipitated at a pH of about 5 for use in suspension formulations intended to give prolonged effect when used, for example, in the eye. It will be appreciated that when using a salt as starting material the incorporation of additional base may not be necessary.

The formulations can be used for optical and/or dermal use and may also find application in other areas, such as in the preparation of suppositories.

The method of the invention and pharmaceutical formulations in accordance with the invention will now be illustrated with reference to the following examples:

EXAMPLE 1

Ophthalmic Suspension of Aciclovir (Multidose)

| Ingredient | Concentration, % w/w |
|---|---|
| Aciclovir Ph. Eur. | 1.00 |
| Polysorbate 80 Ph. Eur | 0.10 |
| Hydrochloric Acid (1N) | 4.55 |
| Carbomer NF/BP (Carbopol 974P) | 0.55 |
| Hydroxyethylcellulose Ph. Eur (Natrosol 250M Pharm) | 0.50 |
| Sodium hydroxide Ph. Eur. | 0.44 |
| Benzalkonium chloride Ph. Eur (50% solution) | 0.01 |
| Purified water Ph. Eur | q.s. to 100 |

The polysorbate 80 is dissolved in water and stirred. The carbomer is added gradually with stirring continued. The cellulose is added and stirring continued. The resulting carbomer dispersion is autoclaved at 121° C. for 15 minutes. The hydrochloric acid (1N) is filter sterilised (0.2 μm), added aseptically to the carbomer dispersion and the acidic mixture homogenised.

About 40% of the sodium hydroxide is dissolved in water to which solution the aciclovir is added and stirred until dissolved. After filter sterilising (0.2 μm), the aciclovir salt is added to the acidic mixture, followed by homogenisation then deaeration. A 10% w/v solution of the remainder of the sodium hydroxide (filter sterilised to 0.2 μm) is then aseptically added with stirring. Finally, the benzalkonium chloride (also filter sterilised to 0.2 μm) is added aseptically with stirring.

EXAMPLE 2

Unpreserved Ophthalmic Suspension (Unit Dose)

The following formulation was prepared in accordance with the method described with respect to Example 1, up to but excluding the final step (addition of benzalkonium chloride):

| Ingredient | Concentration, % w/w |
|---|---|
| Aciclovir | 1.00 |
| Polysorbate 80 | 0.10 |
| Hydrochloric Acid (1N) | 4.55 |
| Carbopol 974P | 0.55 |
| Natrosol 250M Pharm | 0.50 |
| Sodium hydroxide | 0.44 |
| Purified water | q.s. to 100 |

EXAMPLE 3

Aciclovir Suspension vs. H. keratitis

The biological activity of an aciclovir suspension according to Example 1 of the present invention against Herpes keratitis was compared with that of placebo (formulated as for the aciclovir suspension in the absence of the aciclovir) and Zovirax (registered trademark, 3% aciclovir in paraffin-based ointment) using the rabbit eye model. A description of the model may be found in Bull. Soc. Belge Ophtalmol., 186, 109–118, (1979) and Antimicrob. Agents Chemother., 17, 8–12, (1980), both of which are herein incorporated by reference in their entirety.

Ten rabbits were infected in both eyes with a 20 µl inoculum containing 10 e4.5 pfu/ml of TK HSV-1 (McIntyre strain). Four days after infection, 50 µl of placebo or aciclovir suspension, or a 1 cm length of ointment was instilled into the lower fornix of each eye for 5 days. The severity of keratitis was assessed on a scale of 0–5 (0=normal, transparent cornea; 5=total corneal ulceration). The mean keratitis score was recorded as an average daily score for all 20 eyes.

Two studies were undertaken: in the first, the aciclovir suspension was administered 5 and 3 times per day; and in the second, the aciclovir suspension was administered 3 and 1 time(s) per day. The results are shown in the tables below from which it can be seen that the aciclovir suspension administered 5× and 3× was generally superior or similar in performance to Zovirax 5×; and that it exhibited a similar order of efficiency when administered 1×.

Results (to one decimal place)
Study 1 Mean scores of keratitis (n=10)

| DAY | PLACEBO | ZOVIRAX ×5 | SUSPENSION ×5 | SUSPENSION ×3 |
|---|---|---|---|---|
| 0 | 0.55 | 0.65 | 0.49 | 0.49 |
| 1 | 1.26 | 0.53 | 0.26 | 0.31 |
| 2 | 2.02 | 0.64 | 0.21 | 0.19 |
| 3 | 2.32 | 0.54 | 0.09 | 0.12 |
| 4 | 2.15 | 0.39 | 0.10 | 0.05 |
| 5 | 2.20 | 0.48 | 0.04 | 0.04 |

Study 2 Mean scores of keratitis (n=10)

| DAY | PLACEBO | ZOVIRAX ×5 | SUSPENSION ×3 | SUSPENSION ×1 |
|---|---|---|---|---|
| 0 | 0.52 | 0.67 | 0.63 | 0.68 |
| 1 | 1.18 | 0.36 | 0.36 | 0.48 |
| 2 | 2.08 | 0.25 | 0.27 | 0.48 |
| 3 | 2.24 | 0.16 | 0.19 | 0.50 |
| 4 | 2.33 | 0.06 | 0.26 | 0.41 |
| 5 | 2.29 | 0.06 | 0.24 | 0.41 |

EXAMPLE 4

Aciclovir Multidose Formulation

An alternative aciclovir formulation may be prepared using the method described in Example 1 containing the following ingredients in the given concentrations.

| Aciclovir | 1.00% w/w |
|---|---|
| Polysorbate 80 | 0.10% w/w |
| Hydrochloric Acid (1N) | 4.55% w/w |
| Carbopol 974 | 0.55% w/w |
| Natrosol 250M | 0.50% w/w |
| Sodium Hydroxide | 0.44% w/w |
| Benzalkonium Chloride | 0.01% w/w |
| Disodium Edetate | 0.06% w/w |
| Purified Water | to 100% w/w |

EXAMPLE 5

Ganciclovir Multidose Formulation

A multidose formulation containing ganciclovir may be prepared using the method described in Example 1 and containing the following ingredients in the given concentrations.

| Ganciclovir | 1.00% w/w |
|---|---|
| Polysorbate 80 | 0.10% w/w |
| Hydrochloric Acid (1N) | 4.03% w/w |
| Carbopol 974 | 0.55% w/w |
| Natrosol 250M | 0.50% w/w |
| Sodium Hydroxide | 0.42% w/w |
| Benzalkonium Chloride | 0.01% w/w |
| Disodium Edetate | 0.06% w/w |
| Purified Water | to 100% w/w |

EXAMPLE 6

Penciclovir Multidose Formulation

A multidose formulation containing penciclovir may be prepared using the method described in Example 1 and containing the following ingredients in the given concentrations.

| Penciclovir | 1.00% w/w |
|---|---|
| Polysorbate 80 | 0.10% w/w |
| Hydrochloric Acid (1N) | 4.06% w/w |
| Carbopol 974 | 0.55% w/w |
| Natrosol 250M | 0.50% w/w |
| Sodum Hydroxide | 0.42% w/w |
| Benzalkonium Chloride | 0.01% w/w |
| Disodium Edetate | 0.06% w/w |
| Purified Water | to 100% w/w |

EXAMPLE 7

Ganciclovir Unit Dose Formulation

A unit dose formulation containing ganciclovir may be prepared using the method described in Example 1 and containing the following ingredients in the given concentrations.

| | |
|---|---|
| Ganciclovir | 1.00% w/w |
| Polysorbate 80 | 0.10% w/w |
| Hydrochloric Acid (1N) | 4.03% w/w |
| Carbopol 974 | 0.55% w/w |
| Natrosol 250M | 0.50% w/w |
| Sodium Hydroxide | 0.42% w/w |
| Purified Water | to 100% w/w |

EXAMPLE 8

Penciclovir Unit Dose Formulation

A unit dose formulation containing penciclovir may be prepared using the method described in Example 1 and containing the following ingredients in the given concentrations.

| | |
|---|---|
| Penciclovir | 1.00% w/w |
| Polysorbate 80 | 0.10% w/w |
| Hydrochloric Acid (1N) | 4.06% w/w |
| Carbopol 974 | 0.55% w/w |
| Natrosol 250M | 0.50% w/w |
| Sodium Hydroxide | 0.42% w/w |
| Purified Water | to 100% w/w |

What is claimed is:

1. A method of preparing a pharmaceutical formulation for administering to a patient in need thereof a pharmacologically active ingredient which is sparingly soluble in water at the pH acceptable for administration, comprising providing the active ingredient in solution in a pharmacologically-acceptable base, mixing the resulting solution with a pharmacologically-acceptable acid in an amount such that the formulation attains a pH in the range of from about 3.5 to about 8.5, forming therefrom by precipitation a suspension of the active ingredient in which the active ingredient has a mean particle size in the range of from 2 to 10 $\mu$m (number) or 4 to 15 $\mu$m (volume) and a $D_{90}$ (as herein before defined) of the order of 5 to 10 $\mu$m (number), and incorporating a viscosity-enhancing agent in the formulation prior to or during the mixing with acid.

2. A method according to claim 1 further comprising incorporating at least one ion-sensitive, hydrophilic polymer in the formulation prior to or during the mixing with acid.

3. A method according to claim 2 which comprises
   (i) dissolving the active ingredient in base to form a salt solution;
   (ii) forming an aqueous suspension or dispersion of the ion-sensitive, hydrophilic polymer(s) and the viscosity-enhancing agent; and
   (iii) bringing the salt solution, the aqueous suspension or dispersion and the acid into admixture
whereby there is formed a precipitate of microparticles of the active ingredient wherein 90% of the microparticles are of a diameter less than about 10 $\mu$m (number) when measured by a Coulter counter (100 $\mu$m tube).

4. A method according to claim 3 which comprises
   (i) dissolving the active ingredient in base to form a salt solution;
   (ii) forming an acidic dispersion of an ion-sensitive, hydrophilic polymer and a viscosity-enhancing agent in an acid; and
   (iii) mixing the salt solution with the acidic dispersion to produce a precipitate of particles of active ingredient having a particle size $D_{90}$ less than about 16 $\mu$m (volume); and
   (iv) adding sufficient base to produce an aqueous gel having a pH in the range of from about 3.5 to about 8.5.

5. A pharmaceutical composition for administering to a patient in need thereof a pharmacologically active ingredient that is sparingly soluble in water at the pH acceptable for administration and prepared by providing the active ingredient in solution in a pharmacologically-acceptable base, mixing the resulting solution with a pharmacologically-acceptable acid in an amount such that the resulting formulation attains a pH in the range of from about 3.5 to about 8.5, incorporating a viscosity-enhancing agent in the solution prior to mixing with the acid or prior to or during mixing with the acid, and forming therefrom by precipitation a suspension of the active ingredient in which the active ingredient has a mean particle size in the range of from 2 to 10 $\mu$m (number) or 4 to 15 $\mu$m (volume) and a $D_{90}$ (as herein before defined) of the order of 5 to 10 $\mu$m (number).

6. A pharmacological composition according to claim 5 prepared by further incorporating at least one ion-sensitive, hydrophilic polymer in the solution prior to mixing with the acid or during mixing with the acid.

7. A pharmaceutical formulation for administering to a patient in need thereof a pharmacologically active ingredient that is sparingly soluble in water at the pH acceptable for administration and which formulation comprises:
   (a) 0.1–5% w/w of an active ingredient which is capable of being dissolved by a pharmacologically-acceptable base;
   (b) a viscosity-enhancing agent;
   (c) a pharmacologically-acceptable base in which the active ingredient is soluble in an amount sufficient to dissolve substantially all of the active ingredient; and
   (d) a pharmacologically-acceptable acid in an amount such that the formulation has a pH in the range of from about 3.5 to about 8.5; wherein the active ingredient is present in the formulation in the form of a suspension of solid particles which are formed in situ and which have a mean particle size in the range of from 2 to 10 $\mu$m (number) or 4 to 15 $\mu$m (volume) and a $D_{90}$ (as herein before defined) of the order of 5–10 $\mu$m (number).

8. A formulation according to claim 7 which also includes 0.1 to 3% w/w of one of more ion-sensitive hydrophilic polymer(s) and a pharmaceutically acceptable base which is present in an amount sufficient to neutralize the ion-sensitive hydrophilic polymer(s).

9. A pharmaceutical formulation for administering to a patient in need thereof a pharmacologically active ingredient which is sparingly soluble in water at the pH acceptable for administration, which formulation comprises a viscosity-enhancing agent and a suspension of particles of the active ingredient having a mean particle size in the range of from 2 to 10 $\mu$m (number) or 4 to 15 $\mu$m (volume) and a $D_{90}$ (as herein before defined) of the order of 5–10 $\mu$m (number) in an aqueous gel having a pH in the range of from about 3.5 to about 8.5.

10. A method according to claim 2 wherein the or at least one of the ion-sensitive hydrophilic polymers is a cross-linked polyacrylic acid.

11. A method according to claim 2 wherein the ion-sensitive hydrophilic polymer component is present in an amount of from about 0.1 to about 3.0% w/w.

12. A method according to claim 1 wherein the viscosity-enhancing agent is present in the formulation in an amount of from about 0.1 to about 3.0% w/w.

13. A method according to claim 1 where the active ingredient is aciclovir.

14. A pharmaceutical composition according to claim 5 wherein the active ingredient is aciclovir.

15. A pharmaceutical formulation according to claim 7 wherein the active ingredient is aciclovir.

16. The use of a pharmaceutical formulation according to claim 5 in the treatment of an organ of a patient which is sensitive to pH outside the range of 3.5 to 8.5.

17. The use of a pharmaceutical formulation according to claim 5 in the treatment of the eye(s) or skin of a patient.

18. The use of a pharmaceutical formulation according to claim 7 in the treatment of an organ of a patient which is sensitive to pH outside the range of 3.5 to 8.5.

19. The use of a pharmaceutical formulation according to claim 7 in the treatment of the eye(s) or skin of a patient.

20. A pharmaceutical formulation according to claim 9 wherein the suspension particles of the active ingredient has a mean particle size in the range of from 7–9 $\mu$m (number) or 10–16 $\mu$m (volume).

21. A pharmaceutical formulation according to claim 9 wherein the active ingredient is aciclovir.

22. The use of a pharmaceutical formulation according to claim 9 in the treatment of an organ of a patient which is sensitive to pH outside the range of 3.5 to 8.5.

23. The use of a pharmaceutical formulation according to claim 9 in the treatment of the eye(s) or skin of a patient.

* * * * *